United States Patent [19]
Gingold et al.

[11] Patent Number: 5,718,885
[45] Date of Patent: Feb. 17, 1998

[54] RELIEF OF DENTINAL HYPERSENSITIVITY BY SUBMICRON PARTICLES

[75] Inventors: James L. Gingold, Morristown; Kenneth J. Markowitz, Fanwood; Kuo-Chen Yeh, Westfield; Adonis Buelo; James K. Herms, both of Jersey City; Joseph Synodis, Summit, all of N.J.

[73] Assignee: Block Drug Co., Inc., Jersey City, N.J.

[21] Appl. No.: 739,279

[22] Filed: Oct. 29, 1996

Related U.S. Application Data

[63] Continuation of Ser. No. 254,178, Jun. 6, 1994, abandoned.

[51] Int. Cl.$^6$ .............. A61K 7/16; A61K 9/20; A61K 9/68
[52] U.S. Cl. ............ 424/49; 424/435; 424/410; 424/48
[58] Field of Search .......................... 424/49–58

[56] References Cited

U.S. PATENT DOCUMENTS

| | | | |
|---|---|---|---|
| 3,718,584 | 2/1973 | Beste et al. | 252/8.1 |
| 3,998,973 | 12/1976 | Carlson | 424/357 |
| 4,545,923 | 10/1985 | Gradeff et al. | 252/309 |
| 4,647,401 | 3/1987 | Gradeff et al. | 252/309 |
| 4,714,567 | 12/1987 | Roha | 252/315.2 |
| 4,913,840 | 4/1990 | Evans et al. | 252/315.2 |
| 5,030,097 | 7/1991 | Tobey | 433/199.1 |
| 5,049,375 | 9/1991 | Tsujita et al. | 424/52 |
| 5,130,146 | 7/1992 | Tsujita et al. | 424/673 |
| 5,244,651 | 9/1993 | Kayane et al. | 424/57 |
| 5,302,373 | 4/1994 | Giacin et al. | 424/49 |
| 5,330,749 | 7/1994 | Giacin et al. | 424/49 |

OTHER PUBLICATIONS

Abstracts of Eguchi et al. JP 0507 0358 A (Mar. 23, 1993).
Abstracts of Hoburg et al. WO/PCT 93/00884A (Jan. 21, 1993).
Abstracts of Zahrad Nik EP 102200 (Mar. 7, 1984).
Abstracts of Archibold et al. U.S. 4267167 (May 12 1981).

*Primary Examiner*—Shep K. Rose
*Attorney, Agent, or Firm*—Ostrolenk, Faber, Gerb & Soffen, LLP

[57] ABSTRACT

Phosphate-free oral compositions containing cationically charged colloids are effective to treat tooth hypersensitivity.

46 Claims, No Drawings

RELIEF OF DENTINAL HYPERSENSITIVITY BY SUBMICRON PARTICLES

This is a Continuation of application Ser. No. 08/254,178 filed on Jun. 6, 1994 now abandoned.

BACKGROUND OF THE INVENTION

1. Field of the Invention

This invention relates to compositions and methods for treating hypersensitive teeth using materials having reduced abrasive properties.

2. Description of Related Art

Dental hypersensitivity is a frequently encountered problem in dentistry and a very troublesome clinical complaint. Hypersensitivity can cause pain and discomfort as a result of a variety of conditions such as changes in temperature, pressure, chemical or osmotic action. Exposure of the dentin frequently leads to hypersensitivity. Dentin exposure may occur due to abrasion, recession of the gums, attrition, periodontal disease, improper dental care and the like. The usual methods of treating hypersensitive teeth often employ a desensitizing dentifrice or solution.

One approach to desensitizing teeth is to occlude exposed dental tubules. These fluid filled tubules lead from the pulp to the surface of the dentin. When the surface of the tooth is eroded, the dental tubules become exposed to the external environment. The exposed dentinal tubules provide a pathway for the transmission of external stimuli, such as changes in temperature, pressure, ionic gradients and the like, directly to the pulpal nerves causing a strong pain response by the nerve. Blocking the tubules reduces the effects of the external stimuli on the nerve, thereby reducing or eliminating any pain response by the nerve.

Tubule occluding agents may be administered in a variety of ways. Dentifrice compositions, including pastes and gels, may be used, mouthwashes or oral rinses may be used, and professionally applied coatings may also be used to deliver tubule occluding agents to the dentin.

Many agents assumed to be effective in the treatment of sensitive teeth are known. Some of these treatments have been demonstrated to be capable of occluding the dentinal tubules. For example, U.S. Pat. No. 3,122,483 to Rosenthal, issued Feb. 25, 1964, teaches the use of strontium ions as a desensitizing agent. Related patents include U.S. Pat. No. 3,699,221 to Schole et al., issued Oct. 17, 1992; U.S. Pat. No. 4,990,327 to Neirinckx, issued Feb. 5, 1991; and U.S. Pat. No. 5,087,444 to Jackson et al., issued Feb. 11, 1992. U.S. Pat. No. 4,224,310 to Shah, issued Sep. 23, 1992, is directed to Strontium EDTA, while a water soluble strontium and potassium salt in combination is the mentioned by European Application No. 390,456. U.S. Pat. No. 5,015,465 to Straw, issued May 14, 1991, is directed to strontium salts such as acetates, chlorides, nitrates, lactates and bromides. U.S. Pat. No. 4,057,621 to Pashley et al., issued Nov. 8, 1977, and U.S. Pat. No. 4,538,990 also to Pashley, issued Sep. 3, 1985, are directed to the use of an alkaline metal or ammonium oxylate. U.S. Pat. No. 3,863,006 to Hodosh, issued Jan. 28, 1975, is directed to the use of an alkali metal nitrate. Citric acid and sodium citrate are mentioned in U.S. Pat. No. 4,011,309 to Lutz, issued Mar. 8, 1977, while calcium chloride dihydrate, magnesium chloride hexahydrate, sodium chloride and potassium bicarbonate are mentioned in U.S. Pat. No. 3,689,636 to Svajda, issued Sep. 5, 1972. Potassium and strontium nitrate are mentioned in U.S. Pat. No. 4,933,171 to Bristow et al., issued Jun. 12, 1990, while the use of copolymers to form a protective barrier covering the dental tubules is mentioned in U.S. Pat. No. 5,133,957 to Suh et al., issued Jul. 28, 1992. British Patent No. 2,239,601 teaches the combination of an alkaline metal salt with a chloride, nitrate, sulphate or acetate of a group II metal or aluminum or a polymerizable monomer to form a protective coating over the tubules.

The use of particulate materials as desensitizers is also generally known. Thus U.S. Pat. No. 4,992,258 to Mason, issued Feb. 12, 1991, is directed to the use of montmorronlinite clay having a particle size of less than 2 microns as being effective for blocking dental tubules using a dentin hydraulic conductance chamber. In U.S. Pat. No. 4,645,622 to Nakashima et al., issued Feb. 24, 1987, the dental tubules, which are indicated to have a diameter in the range of about 1-3 microns, are occluded or constricted by employing soluble aluminum carboxylate compounds. The other components of the composition are selected so as not to reduce the number of available aluminum ions. Alumina in a concentration of 5-50% is suggested as an abrasive. U.S. Pat. No. 4,634,589 to Scheller, issued Jan. 6, 1987, is directed to the use of apatite having an average particle size of less than 8 microns, preferably less than 4 microns, as a desensitizer to occlude dentinal tubules. Apatite is composed of calcium phosphate, calcium phosphate fluoride, and calcium carbonate phosphate. The use of amorphous calcium compounds applied to dentinal tissue to rapidly form apatite in situ, thus remineralizing the teeth and purportedly reducing dentinal hypersensitivity, is taught in U.S. Pat. No. 5,037,639 to Tung, issued Aug. 6, 1991.

The use of small particle sized materials in dental compositions for a variety of purposes, other than desensitization, is known. As an example, U.S. Pat. No. 4,612,191 to Yeh et al., issued Sep. 16, 1986, is directed to the use of a combination of anhydrous aluminum silicate (available commercially as Kaolin or Kaopolite) having a particle size of less than 1 micron and silica particles for a stain removal abrasive system. U.K. Patent No. 1,449,317 shows 0.1–50 micron polymer particles in a low abrasive dentifrice. Similarly, U.S. Pat. No. 4,986,981 to Glace et al., issued Jan. 22, 1981, discloses a low abrasion toothpaste for removing plaque, mucin and tartar, whose abrasive system includes 1 micron alumina. Use of 1–15 micron hydroxyapatite as an abrasive in an oral desensitizer composition is discussed in U.S. Pat. No. 4,933,171 to Bristow et al., issued Jun. 12, 1990.

U.S. Pat. No. 5,244,651 to Kayane, issued Sep. 14, 1993, is directed to a method of desensitizing hypersensitive dentin. The method comprises treating teeth with a combination of a salt of a polyvalent metal and a polyol phosphate. This combination produces a colloid of metal hydroxides. Apparently, the colloid is stabilized by the phosphate compound. The compound is prepared by combining the chloride, sulfate, or nitrate salt of magnesium, strontium, barium, zinc, iron titanium, aluminum, chromium, manganese, copper, nickel, cobalt, bismuth, tin, vanadium, molybdenum, niobium, zirconium, antimony, indium, or a lanthanoid with a polyol phosphate in acidic or neutral aqueous medium. The medium is then adjusted to neutral pH. Preferred phosphates include glycerol phosphate.

Despite the time honored use of alumina particles in dental compositions as abrasives, desensitization properties have not been directly attributed to this material. (See Mostafa, et al., J. Dent. Res. 1983; 62 (Spec. Issue): 433 (Abstr. 165). Mostafa et al. have shown that abrasive materials (alumina, silica calcium carbonate etc.) interact with dentin as seen in SEM photomicrographs and concluded that abrasives may have an important role in reducing dentin hypersensitivity by blockage of tubules. But, applicants have discovered that abrasive and polishing grade alumina, aluminum oxide and aluminum silicate are ineffective for reducing dentinal fluid flow through dentin disks. It was therefore surprising and unexpected to discover that cationically charged colloidal particles, including alumina, were effective in reducing dentinal flow by occluding the dentinal tubules.

Some agents are known to form mineral deposits on the surfaces of the exposed dental tubules while in some cases, the abrasive action from brushing may cause a smear layer to form over the surface of the tooth and thus plug up the open tubules. The accumulation of particulate matter from the interstitial fluid passing through the dental tubules or remineralization within the tubules can also cause a natural occlusion of the tubules.

One difficulty presented by using occlusive dentifrice treatments for hypersensitive teeth is that the act of brushing the teeth, particularly with an abrasive dentifrice, can dislodge occlusive materials from the tubules, especially newly added materials residing at the entrance to the tubules.

SUMMARY OF THE INVENTION

The principal object of the present invention therefore is to provide a new dentinal desensitizing agent and compositions containing that agent.

An additional object of the invention is to provide a composition having reduced abrasion levels to thereby reduce the deleterious effect of highly abrasive compositions on tubule occlusion.

Still another object of the invention is to provide a method for treating hypersensitive teeth with the desensitizing agent of the invention.

One advantage of the invention is that the desensitizing agent of the invention may also act as an abrasion reducing agent.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a composition containing cationically charged colloidal particles for treating hypersensitive teeth.

To further achieve the foregoing objects and in accordance with the purpose of the invention, the invention further provides a method for treating a hypersensitive tooth by applying a composition containing cationically charged colloidal particles to at least the affected region of the tooth.

DESCRIPTION OF THE INVENTION

Reference will now be made in detail to the presently preferred embodiments of the invention.

In accordance with the present invention, cationically charged colloidal particles are used as a dental desensitizing agent. The particles may be employed in conjunction with a dentally acceptable carrier and can be formulated into any type of oral composition such as an aqueous suspension, dentifrice, gel, mouthwash, lozenge, buccal adhesive patch, gum or other oral composition whose use on a periodic basis can provide relief from the pain and discomfort of hypersensitive teeth.

Preferably the particles of the invention are selected from compounds comprising metals from groups IB, IIA, IIB, IIIA, IIIB, IVB, VA, VB, VIA, VIB, VIIB, and VIIIB of the Periodic Table, including the Lanthanides. For economic reasons, it is preferred that the metals are selected from commonly occurring compounds, such as alumina, and the compounds should be non-toxic. Preferably the metals are selected from the group consisting of: Y, Ti, V, Cr, Mn, Fe, Co, Cu, Zn, Al, Mg, Ca, Sr, Ba, Zr, Ag, Sn, Bi, W, Ce, La, Pr, Nd, and Sc. More preferably, the metals are selected from the group consisting of: Y, Ce, Al, and Zr. Most preferably, the metal is aluminum or zirconium.

The compounds must be capable of forming colloids in aqueous environments, either alone or in conjunction with suitable buffers. The colloids formed from these compounds must also be capable of holding a cationic charge in the aqueous environments ordinarily found in the oral cavity. Preferably, the compounds are relatively less expensive, stable, non-toxic compounds, like some halides, silicates, acetates, oxides and hydroxides. Most preferably, the compounds are oxides.

Cationically charged colloidal alumina has heretofore been used for a variety of applications such as, for instance, a binder in glass and ceramic systems, a catalyst support, a reinforcing agent, a dust or dirt repellent and in waterproofing compositions. This type of alumina is commercially available and the submicron particles have usually been surface treated so as to impart a positive surface charge thereon. Any of these commercially available materials can be employed in the process and products of the present invention as long as the colloid is dentally acceptable. One example of a commercially available product is that sold under the trademark Nalco 8676 and this alumina has an average particle size of about 2 nm (0.002 µm). The alumina can also be in the form of a coating on another material such as silica, in which case the submicron size is of the entire particle and not just the alumina. An example is sold under the trademark Nalco 1056 and is alumina-coated silica particles whose average size is 20 nm (0.02 µm). The two named commercially available products are in the form of an aqueous colloidal dispersion of the submicron alumina particles. Such aqueous dispersions can often be used as such in order to formulate the dental compositions of the present invention and it is not necessary to separate the particles of alumina from the dispersion.

In general, the particle size is submicron and is usually up to about 0.1 µm. The colloid particles often are in the range from about 0.001 to about 0.2 µm and preferably from about 0.001 to about 0.025 µm.

The compound is incorporated into the dental composition in a desensitizing effective amount. This will vary depending on the particular type of oral composition and other materials present but most often, the agent will be an amount of about 0.1 to 10%, usually about 1 to 5% and most preferably about 3 to about 5%. Larger amounts of the compound can also be employed if so desired.

The compound can be incorporated into any type of oral dental composition as long as the cationic surface charge of the desensitizing agent is not completely neutralized. It is preferred that the amount of neutralization of that charge be minimal. By combining the compound with a suitable dentally acceptable carrier, the dental oral composition can take the form of a dentifrice, mouthwash, lozenge, buccal adhesive patch, gel or gum and the like. The other ingredients used to formulate such compositions and the procedures employed are well known and commonly used in preparing these oral compositions. Thus, for instance, it is possible to incorporate a fluoride source into the oral composition and it is also possible to formulate the oral compositions in conjunction with additional desensitizing agents. Such additional desensitizing agents include, without limitation, strontium chloride and other strontium containing compounds, potassium nitrate, sodium silicofluoride, zinc chloride, potassium chloride, potassium bicarbonate and glycerine. In toothpaste formulations, the submicron compound of the invention generally does not provide sufficient abrasive/polishing activity and therefore the use of known abrasives such as larger particle sized alumina or silica will normally be incorporated in the composition.

But, one surprising advantage of cationically charged colloidal alumina is that its presence can materially reduce the abrasion levels of dentifrices. This reduced abrasion helps to offset loss of some of the occluding material that would otherwise be lost through abrasive scouring action during brushing. Thus, added abrasives will not have as direct an effect on abrasion of the dentin as in ordinary dentifrices.

In order to further illustrate the present invention, various non-limiting examples are set forth below. In these examples, as throughout the specification and claims, all temperatures are in degrees centigrade and all parts and percentages are by weight unless otherwise indicated.

EXAMPLES 1–4

In order to test the desensitizing properties of potential desensitizing agents, four different aluminum-containing particles were mixed with water and the resulting oral compositions tested using the method described in Pashley, "Dentin permeability: Theory and practice", *Experimental Endodontics*, Spangberg, ed. CRC Press 1989). This test measures the flow of fluid through a sliced dentin disk. A treatment that will reduce the flow through the disk can also result in reduced dentinal hypersensitivity for people using the treatment.

A caries-free tooth is sliced to obtain a 0.4 to 0.6 mm thick dentin disk. The disk is mounted on a split chamber device as described in the Journal of Dental Research, 57:187, 1978. The initial flow of fluid through the disk is measured and then the disk is exposed to human saliva and treated by brushing with one of the desensitizing treatments. After brushing, the flow rate is again measured and the reduction in flow is calculated from these measurements. The results are set out in Table 1.

TABLE 1

| Particulate | Particle Size | Concentration Percent | Flow Reduction |
|---|---|---|---|
| Aluminum silicate | 1.0 μm | 5% | 9.5% |
| Aluminum hydroxide | 0.5 μm | 10% | 24.1% |
| Uncharged alumina | 0.013 μm | 17% | 19.3% |
| Cationic alumina | 0.002 μm | 5% | 93.4% |

These results confirm that the presence of a cationic charge on submicron alumina drastically reduces tubular flow even though the concentration of the particulate had been reduced by a factor greater than three.

EXAMPLES 5–13

Example 4 was repeated varying the concentration of the alumina and adjusting the pH with sodium hydroxide. The results are set out in Table 2.

TABLE 2

| pH | Concentration % | Flow Reduction % |
|---|---|---|
| 5 | 0.13 | 46.3 |
| 5 | 1.0 | 86.4 |
| 5 | 2.4 | 88.2 |
| 5 | 8 | 89.8 |
| 5.5 | 0.98 | 84.1 |
| 6 | 0.22 | 38.6 |
| 6 | 0.48 | 51.8 |
| 6 | 0.95 | 65.8 |

EXAMPLES 14–18

Example 5 was repeated with 0.02 micron alumina-coated silica particles. The results are set out in Table 3.

TABLE 3

| pH | Concentration % | Flow Reduction % |
|---|---|---|
| 8 | 15 | 37.4 |
| 4.5 | 15 | 90.5 |
| 4 | 15 | 96.2 |
| 5 | 22.0 | 28.5 |
| 3.5 | 30.0 | 100 |

EXAMPLE 19

A desensitizing solution is made from the following ingredients:

| INGREDIENT | WEIGHT % (approx.) |
|---|---|
| Colloidal Dispersion of alumina (10%) | 30% |
| Sodium Chloride | 0.6% |
| Water | 69.4% |

EXAMPLE 20

A desensitizing mouth wash is made from the following ingredients:

| INGREDIENT | WEIGHT % (approx.) |
|---|---|
| Colloidal Dispersion of alumina (10%) | 25% |
| Potassium Nitrate | 5% |
| Nonionic Surfactant (Pluronic F-127) | 5% |
| Ethanol | 10% |
| Glycerin | 10% |
| Sodium Saccharin, Flavor | 0.1% |
| Preservative, Dyes | |

EXAMPLE 21

A desensitizing chewing gum is prepared from the following ingredients:

| INGREDIENT | WEIGHT % (approx.) |
|---|---|
| Chewing Gum Base | 24.64% |
| Glycerin | 1% |
| Calcium Saccharin | 0.06% |
| Sorbitol (Powder) | 53.5% |
| Lycasin | 13% |

| INGREDIENT | WEIGHT % (approx.) |
|---|---|
| Lecithin | 0.8% |
| Flavor | 1% |
| Colloidal Dispersion of Alumina (10%) | 6% |

EXAMPLE 22

A desensitizing lozenge is prepared from the following ingredients:

| INGREDIENT | WEIGHT % (approx.) |
|---|---|
| Sorbitol | 86.5% |
| Xylitol | 6% |
| Citric Acid | 0.4% |
| Colloidal Dispersion of Alumina (10%) | 7% |
| Flavor | 0.1% |

EXAMPLE 23

A desensitizing topical gel is prepared from the following ingredients:

| INGREDIENT | WEIGHT % (approx.) |
|---|---|
| Water | 33.4% |
| Glycerin | 6% |
| Sorbitol | 6% |
| Colloidal Dispersion of Alumina (10%) | 24% |
| Potassium Nitrate | 5.0% |
| Pluronic F-127 | 25% |
| Flavor, Preservative and Dye | 0.6% |

EXAMPLE 24

A desensitizing dentifrice is prepared from the following ingredients:

| INGREDIENT | WEIGHT % (approx.) |
|---|---|
| Water | 38% |
| Potassium Nitrate | 5.0% |
| Sylodent 750 (hydrated silica) | 0.2% |
| Sodium Fluoride | 0.2% |
| Carboxymethyl Cellulose | 2.0% |
| Glycerin | 20% |
| GAFQUAT 755N (20%) | 4.0% |
| Colloidal Dispersion of Alumina (10%) | 30% |
| Flavor and Preservatives | 0.6% |

EXAMPLE 25

In order to demonstrate that the colloidal alumina particles reduce abrasion, six laboratory batch dentifrices were prepared using various desensitizing dentifrice formulations. 10% by weight Tixocil® abrasive, a silica abrasive manufactured by Rhone-Poulenc, was added to each batch to increase the amount of abrasives in the dentifrice and thereby to accentuate the effect of the colloidal alumina on the system. 10% by weight Nalco beads were added to three of the batches and all six batches were measured, using the standard test, for "Radioactive Dentin Abrasion" (RDA). This value is reported in Tables 4 and 5 as "A.I.," the "abrasion index." The results are reported with their associated Standard Error of Mean values.

TABLE 4

| FORMULA DESCRIPTION | A.I. Index (± SEM) | RANGE |
|---|---|---|
| Sensodyne SC type 10% Tixosil 73 10% Nalco | 31 ± 1 | 29–33 |
| Sensodyne SC type 10% Tixosil 73 | 37 ± 4 | 24–52 |
| KNO₃/MFP T.P. 10% Tixosil 73, 10% Nalco | 51 ± 2 | 42–56 |
| KNO₃/MFP T.P. 10% Tixosil 73 | 69 ± 3 | 57–78 |
| KNO₃/NaF T.P. 10% Tixosil 73 10% Nalco | 23 ± 1 | 18–30 |
| KNO3/NaF T.P. 10% Tixosil 73 | 62 ± 2 | 54–69 |

For clarity, the data set out in Table 4 is summarized in Table 5 and compared against tests run on Crest® brand Regular Flavor toothpaste.

TABLE 5

| FORMULATION | A.I. ± SEM WITHOUT NALCO | A.I. ± SEM WITH NALCO |
|---|---|---|
| KNO₃/MFP/TIXOSIL 73 | 69 ± 3 | 51 ± 2 |
| KNO₃/NaF/TIXOSIL 73 | 62 ± 2 | 23 ± 1 |
| SrCl₂.6H₂O/TIXOSIL 73 | 37 ± 4 | 31 ± 1 |
| CREST | 115 ± 1 | — |

EXAMPLE 26

Dentin flow reduction examples similar to those carried out on colloidal alumina as set forth in Example 1, were carried out on 5–10 nm particle size zirconia, $ZrO_2$, obtained from P.Q. corporation, and sold under the trade name NYACOL. The results are set out in Table 6.

TABLE 6

| Solution Strength | Dentin Flow Reduction |
|---|---|
| 20.0% | 98.5% |
| 2.0% | 91.4% |
| 0.5% | 83.8% |
| 0.25% | 77.2% |
| 0.1% | 14.0% |

EXAMPLE 27

An dentifrice was prepared to demonstrate the utility of one embodiment of the invention. The dentifrice composition set out below provided a flow reduction of 74.2%.

| Dentifrice Ingredient | Weight Percent (approx.) |
|---|---|
| Water | 30.9% |
| Potassium chloride | 3.75% |
| Colloidal zirconia acetate solution, (35%) | 10.0% |
| Glycine | 10.0% |
| Sorbitol solution (70%) | 12.0% |
| Fumed silica | 1.0% |
| Hydrated silica | 12.0% |

-continued

| Dentifrice Ingredient | Weight Percent (approx.) |
|---|---|
| Glycerin | 12.0% |
| Hydroxyethyl cellulose | 1.6% |
| Cocamidopropyl betaine | 5.0% |
| Flavor | 1.5% |
| Sodium fluoride | 0.243% |

EXAMPLE 28

A buffered paste was prepared and tested in accordance with the procedure set forth in Example 1. The paste showed a flow reduction of 95%. The formulation of the buffered paste is set forth below.

| Buffered Paste Ingredient | Weight Percent |
|---|---|
| Colloidal zirconia acetate solution, (35%) | 10% |
| Glycine | 10% |
| Sorbitol solution (70%) | 4.3% |
| Amphoteric surfactant | 3% |
| Kaopolite | 15% |
| Hydrated silica abrasive | 20% |
| Water | 37.5% |

EXAMPLE 29

NYACOL Colloidal yttria, also obtained from P.Q. Corporation, was tested in accordance with the procedure set forth in Example 1 to determine its tubule blocking abilities. A colloidal solution was prepared containing the following ingredients:

| Ingredient | Weight Percent |
|---|---|
| Yttria (yttrium oxide $Y_2O_3$) | 4.2% |
| Potassium nitrate | 5.0% |
| Water | 90% |

The Yttria had a particle size of about 5 nm and displayed a flow reduction of 75.2%

EXAMPLE 30

NYACOL Colloidal ceria also obtained from P.Q. Corporation was tested in accordance with the procedure set forth in Example 1 to determine its tubule blocking abilities. A buffered colloidal solution was prepared containing the following ingredients:

| Ingredient | Weight Percent |
|---|---|
| Ceria (cerium oxide $CeO_2$) | 4.0% |
| Glycine | 10.0% |
| Potassium nitrate | 5.0% |
| Water | 80.75% |

The ceria had a particle size of about 15 nm and displayed a flow reduction of 75.6%.

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. In a composition for treating hypersensitive teeth containing a desensitizing amount of a desensitizing agent and a carrier therefor, the improvement comprising the composition being phosphate-free and the desensitizing agent comprising a cationically charged colloid.

2. The composition of claim 1, wherein said colloid comprises a metal compound selected from the group consisting of: metals of groups IB, IIA, IIB, IIIA, IIIB, IVA, IVB, VA, VB, VIB, VIIB, and VIIIB of the Periodic Table, and the Lanthanides.

3. The composition of claim 2, wherein said colloid comprises a metal compound selected from the group consisting of: Mg, Al, Ca, Sc, Ti, V, Mn, Fe, Co, Cu, Zn, Sr, Y, Zr, Ag, Sn, La, Ce, Pr, Nd, Bi and W compounds.

4. The composition of claim 3, wherein said colloid comprises a metal compound selected from the group consisting of: Y, Ce, Al, and Zr compounds.

5. The composition of claim 4, wherein said colloid comprises an aluminum compound.

6. The composition of claim 2, wherein said colloid comprises a metal oxide.

7. The composition of claim 2, wherein said colloid comprises a metal halide, oxide, hydroxide, silicate or acetate.

8. The composition of claim 1, wherein said carrier is selected from the group consisting of: aqueous suspensions, dentifrices, gels, mouthwashes, lozenges, buccal adhesive patches, and chewing gums.

9. The composition of claim 1, further comprising a second desensitizing agent.

10. The composition of claim 9, wherein said second desensitizing agent comprises a desensitizing salt.

11. The composition of claim 10, wherein said desensitizing salt is selected from the group consisting of desensitizing strontium salts and desensitizing potassium salts.

12. The composition of claim 1, wherein the particle size of said cationically charged colloid is from about 0.001 µm to about 0.2 µm.

13. The composition of claim 12, wherein the particle size of said cationically charged colloid is from about 0.001 µm to about 0.025 µm.

14. The composition of claim 13, wherein said cationically charged colloid comprises up to about 10% by weight of said composition.

15. The composition of claim 14, wherein said cationically charged colloid comprises from about 1% by weight to about 3% by weight of said composition.

16. A method for treating hypersensitive tooth comprising the step of applying to the surface of said tooth a composition containing a desensitizing amount of a desensitizing agent and a carrier therefor, the improvement comprising the composition being phosphate-free and the desensitizing agent comprising an amount of cationically charged colloid sufficient to at least partially desensitize said tooth.

17. The method of claim 16, wherein said carrier is selected from the group consisting of: aqueous suspensions, dentifrices, gels, mouthwashes, lozenges, buccal adhesive patches, and chewing gums.

18. The method of claim 16, further comprising a second desensitizing agent.

19. The method of claim 18, wherein said second desensitizing agent comprises a desensitizing salt.

20. The method of claim 19, wherein said desensitizing salt is selected from the group consisting of desensitizing strontium salts and desensitizing potassium salts.

21. The method of claim 16, wherein the particle size of said cationically charged colloid is from about 0.001 μm to about 0.2 μm.

22. The method of claim 21, wherein the particle size of said cationically charged colloid is from about 0.001 μm to about 0.025 μm.

23. The method of claim 16, wherein said cationically charged colloid comprises up to about 10% by weight of said composition.

24. The method of claims 23, wherein said cationically charged colloid comprises from about 1% by weight to about 3% by weight of said composition.

25. A method for manufacturing a treatment for hypersensitive teeth containing a desensitizing agent and a carrier comprising the step of suspending a desensitizing effective amount of phosphate-free cationically charged colloid as the desensitizer in a suitable phosphate-free carrier to form a desensitizing composition.

26. The method of claim 25, wherein said carrier is selected from the group consisting of: aqueous suspensions, dentifrices, gels, mouthwashes, lozenges, buccal adhesive patches, and chewing gums.

27. The method of claim 25, further comprising the step of incorporating a second desensitizing agent into said composition.

28. The method of claim 27, wherein said second desensitizing agent comprises a desensitizing salt.

29. The method of claim 28, wherein said desensitizing salt is selected from the group consisting of desensitizing strontium salts and desensitizing potassium salts.

30. The method of claim 25, wherein the particle size of said cationically charged colloid is from about 0.001 μm to about 0.2 μm.

31. The method of claim 30, wherein the particle size of said cationically charged colloid is from about 0.001 μm to about 0.025 μm.

32. The method of claim 25, wherein said cationically charged colloid comprises up to about 10% by weight of said composition.

33. The method of claim 32, wherein said cationically charged colloid comprises from about 1% by weight to about 3% by weight of said composition.

34. A method for achieving an at least partial desensitizing effect to at least one hypersensitive tooth of a patient comprising administering an effective amount of a phosphate-free composition containing a desensitizing amount of a cationically charged colloid as desensitizing agent and a carrier therefor to said tooth.

35. The method of claim 34, wherein the particle size of said cationically charged colloid is from about 0.001 μm to about 0.2 μm.

36. The method of claim 35, wherein the particle size of the colloid is from about 0.001 to about 0.025 μm.

37. The method of claim 35, wherein said cationically charged colloid comprises up to 10% by weight of an oral composition.

38. The method of claim 35, wherein said cationically charged colloid comprises from about 1% by weight to about 3% by weight of said oral composition.

39. The method of claim 37, wherein said oral composition is in the form of an aqueous suspension, dentifrice, mouthwash, gel, chewing gum, lozenge or buccal adhesive patch.

40. In a method of desensitizing hypersensitive teeth, utilizing a phosphate-free cationically charged colloid in a desensitizing amount as a desensitizing agent.

41. A dentifrice containing a desensitizing amount of a desensitizing agent and a carrier therefor, wherein the composition is phosphate-free and the desensitizing agent comprising a cationically charged colloid selected from the group consisting of alumina, zirconia, ceria and yttria.

42. A oral rinse containing a desensitizing amount of a desensitizing agent and a carrier therefor, wherein the composition is phosphate-free and the desensitizing agent comprising a cationically charged colloid selected from the group consisting of alumina, zirconia, ceria and yttria.

43. A mouthwash containing a desensitizing amount of a desensitizing agent and a carrier therefor, wherein the composition is phosphate-free and the desensitizing agent comprising a cationically charged colloid selected from the group consisting of alumina, zirconia, ceria and yttria.

44. A desensitizing sealant containing a desensitizing amount of a desensitizing agent and a carrier therefor, wherein the composition is phosphate-free and the desensitizing agent comprising a cationically charged colloid selected from the group consisting of alumina, zirconia, ceria and yttria.

45. The dentifrice of claim 41, wherein the colloid is alumina and the dentifrice contains potassium nitrate as a second desensitizing agent.

46. A method of achieving an at least partial desensitizing effect to at least one hypersensitive tooth of a patient comprising administering an effective amount of the dentifrice of claim 45 to said tooth.

* * * * *